United States Patent
Kusens

(10) Patent No.: US 8,571,894 B1
(45) Date of Patent: Oct. 29, 2013

(54) METHOD AND PROCESS FOR OBTAINING CONSENT TO ACCESS AND POPULATE A PERSONAL HEALTH RECORD

(75) Inventor: Bruce Howard Kusens, North Miami Beach, FL (US)

(73) Assignee: Intermedhx, LLC, Nashville, TN (US)

( * ) Notice: Subject to any disclaimer, the term of this patent is extended or adjusted under 35 U.S.C. 154(b) by 106 days.

(21) Appl. No.: 13/167,691

(22) Filed: Jun. 23, 2011

Related U.S. Application Data

(60) Provisional application No. 61/358,072, filed on Jun. 24, 2010.

(51) Int. Cl.
*G06F 19/00* (2011.01)
(52) U.S. Cl.
USPC .......................................................... 705/3
(58) Field of Classification Search
USPC ...................... 705/3; 707/9; 713/166; 378/62
See application file for complete search history.

(56) References Cited

U.S. PATENT DOCUMENTS

| | | | |
|---|---|---|---|
| 2008/0028214 A1* | 1/2008 | Tafoya et al. | 713/166 |
| 2009/0327297 A1* | 12/2009 | Deobhakta et al. | 707/9 |
| 2011/0122995 A1* | 5/2011 | Ferro, Jr. | 378/62 |
| 2011/0202370 A1* | 8/2011 | Green, III et al. | 705/3 |

* cited by examiner

*Primary Examiner* — John Pauls
(74) *Attorney, Agent, or Firm* — Daniel S. Polley, P.A.

(57) ABSTRACT

An electronic method and system for obtaining consent to access and populate a personal health record is disclosed. The system and method allows healthcare providers to obtain consent and automatically create and/or populate a personal health record chosen by a patient. The system and method also allows for information from billing records concerning the patient or the patient's visit to be extracted to create a billing file which can be electronically sent for importing into the patient's personal health record.

15 Claims, 3 Drawing Sheets

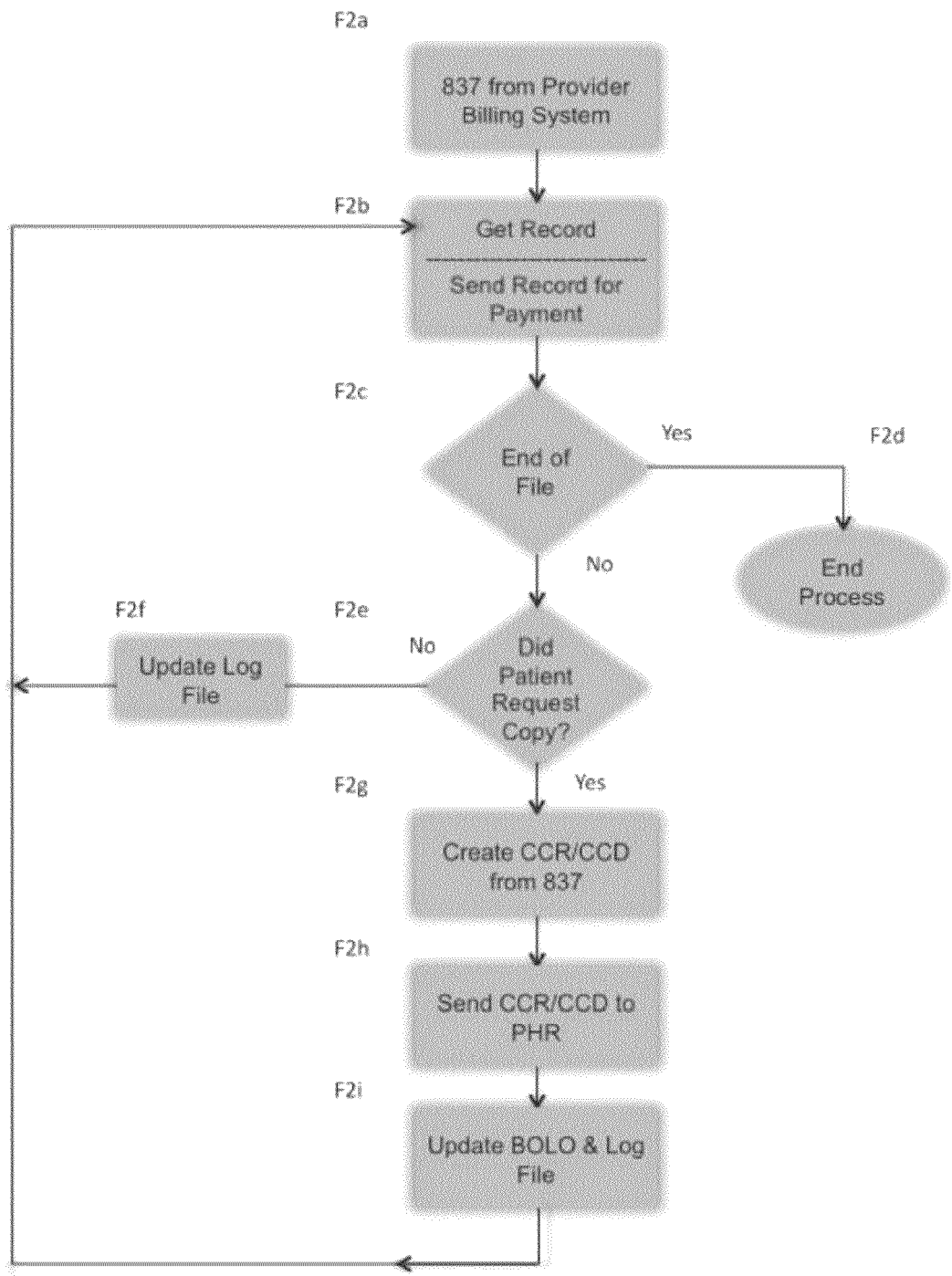
FIGURE 2: Billing File Intercept and PHR Update Process

METHOD AND PROCESS FOR OBTAINING CONSENT TO ACCESS AND POPULATE A PERSONAL HEALTH RECORD

This application claims the benefit of and priority to U.S. Application Ser. No. 61/358,072, filed Jun. 24, 2010, which is incorporated by reference in its entirety.

FIELD OF THE INVENTION

The invention relates generally to personal health records and specifically to electronic method and system for obtaining consent to access and populate a personal health record.

BACKGROUND OF THE INVENTION

In the current environment, no centralized storage of clinical health records exists for those residing in the United States. Rather, these records are stored in hard copy or electronic format in numerous locations and on a large variety of disparate systems. Timely and secure access to a patient's clinical health record for the purpose of providing medical care is a necessity to providing the best clinical care possible.

One such type of clinical record storage is a personal health record. (PHR). Unlike electronic health records maintained by healthcare providers, a PHR is typically maintained in part by the patient with the patient also having full control of access to the PHR. A study released in April 2010 by the California Healthcare Foundation titles "Consumers and Health Information Technology: A National Survey" reports that PHR usage in the U.S is currently at 7% of the population. Although this number has doubled over the past two years, the vast majority of the population does not maintain a personal health record. The California Healthcare Foundation report found that of those without a PHR, 58% would be interested in using one provided by their healthcare providers.

SUMMARY OF THE INVENTION

The present invention generally provides for a system and method that allows healthcare providers to obtain consent and automatically create and/or populate a personal health record chosen by a patient. For purposes of explanation, and not in any limiting sense, the following definitions will be used.

| 1. Definitions | |
|---|---|
| 837 | A HIPAA compliant electronic data format utilized for the purposes of billing payers for healthcare services rendered to its members. However, this format is not considered limiting and other HIPAA and non-HIPAA compliant electronic data formats can be used and are considered within the scope of the invention. |
| Government Issued Identification Card | An identification card issued by a governmental authority in the United States including but not limited to Driver's Licenses, Military Identification cards, Student Identification cards, State Identification cards, and Passports. |
| Clinical Health Record (CCR or CCD) | A record of medical care for a given patient including but not limited to Allergies, Immunizations, Medication History, Lab Results, Radiological Readings, Procedure History, Diagnosis History, Surgical History, information maintained in a Personal Health Records and any other relevant information. |
| Personal Health Record (PHR) | A patient maintained record of medical care history such as those available via the internet or computer USB flash drive. |

| 1. Definitions -continued | |
|---|---|
| Clinical Information System | Computer system and software utilized by a Provider (Hospital, Physician Office, Clinics, etc) to store demographic, clinical and financial data related to its patients. |
| BOLO File | Be On The Lookout for File. This file records decisions made by a user relating to the existence of a PHR or if the patient wants to create one. It is also examined during the billing stage to determine if a record copy should be sent to the patient's PHR. It also serves as a log recording the outcome of decisions regarding the Patients utilization of a PHR |

BRIEF DESCRIPTION OF THE DRAWINGS

FIG. 2 shows the workflow for identifying and processing those claims for which a patient has requested their PHR be updated.

DETAILED DESCRIPTION OF THE PREFERRED EMBODIMENT

Figure 1A:
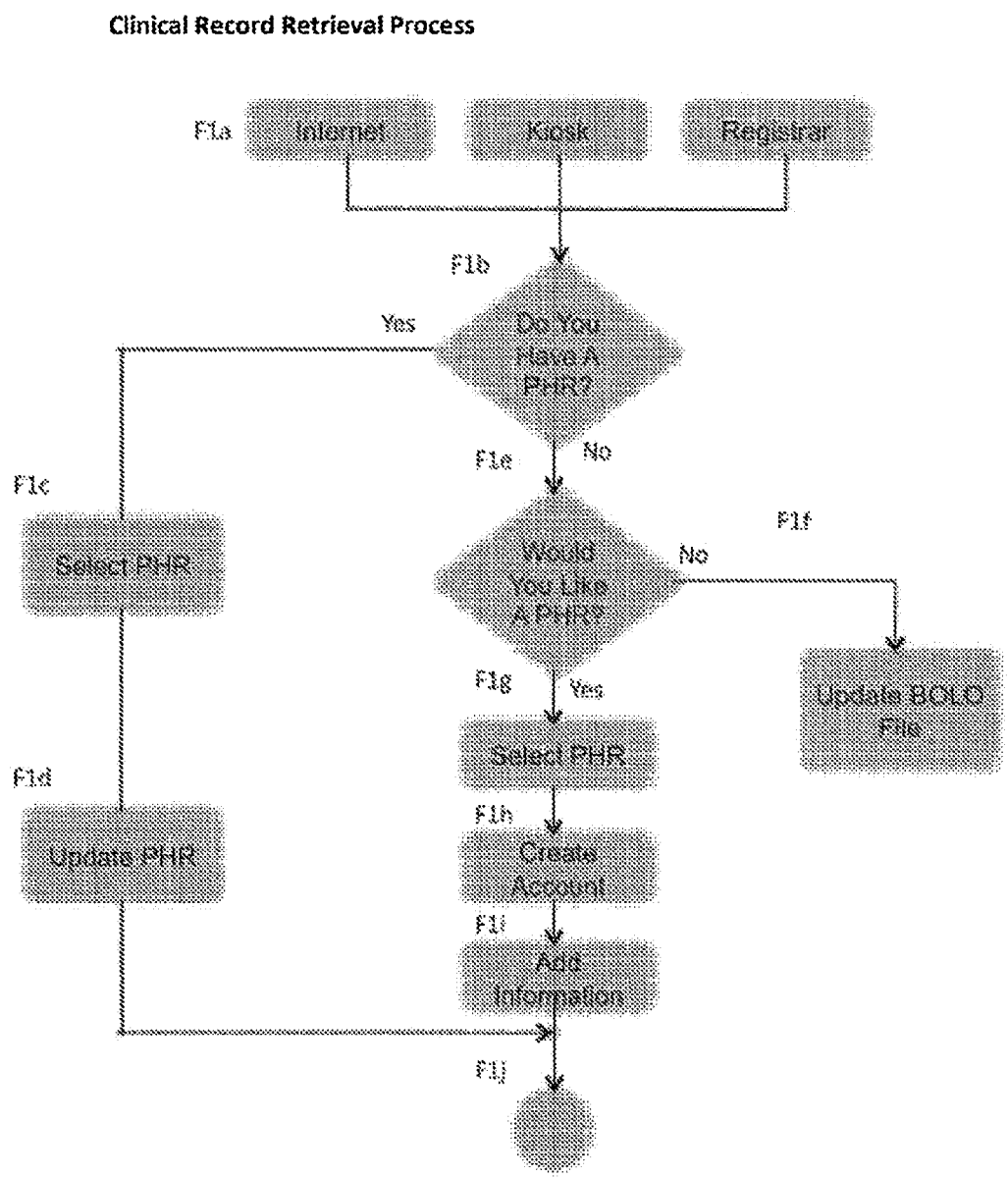
FIG. 1 shows the workflow for determining if a PHR exists and if consent is given to populate it.
Figure 1B:
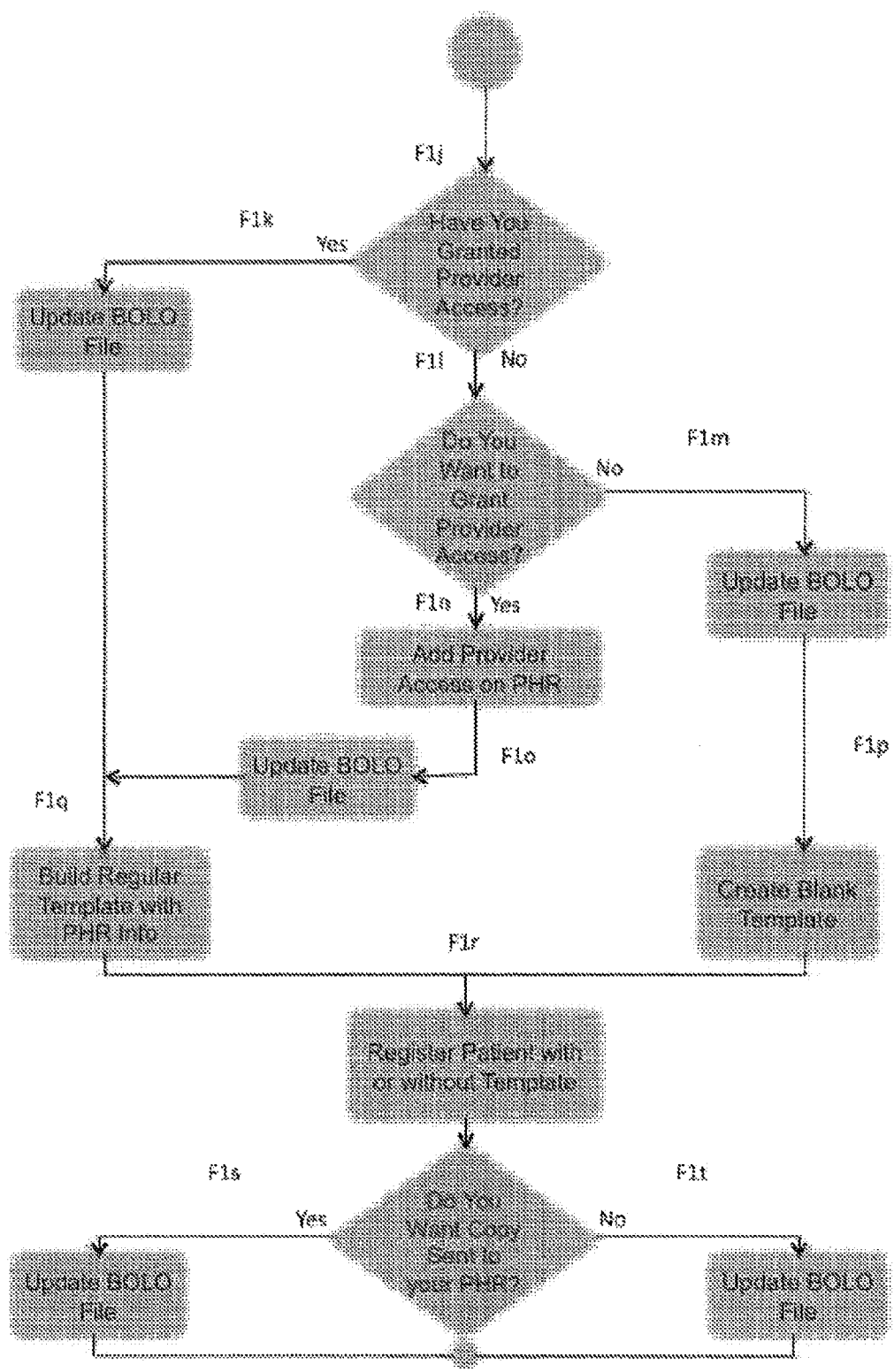

The figures illustrate the various the workflow and decisions made by the present invention system and method. At step F1a a patient attempts to register for healthcare services, preferably, though not limiting, via an Internet Portal, Self-Service Kiosk, or with the Registrar at the provider. Though not considered limiting, this task can be preferably performed at the time of arrival/check-in if performed by the Registrar or the Self-Service Kiosk.

At step F1b the patient is asked to indicate whether or not he/she currently has a PHR. At step F1c if the patient indicates in step F1b that a PHR exists, such as, but not limited to, MedicAlert, Google Health, Quicken Health, Microsoft Health Vault, etc., the patient is asked to select the specific PHR that he/she has for his or her PHR. At step F1d after selecting the appropriate PHR, the patient is given the opportunity to update any information in the PHR. The patient may change any information, such as, but not limited to, address, phone numbers, insurance, allergies, contact, emergency contacts, etc.

If the patient does not currently have a PHR, at step F1e the patient is asked if he/she wants to create one now. If the patient does not have and does not want to create a PHR, the BOLO file is updated to reflect the patient's choices at step F1f. If the patient would like to create PHR, at step F1g a screen with popular MIR systems is presented to the patient to select which one he/she would like to create such as but not limited to, MedicAlert, Google Health, Quicken Health, Microsoft Health Vault, etc. At step F1h the patient is asked to provide information necessary to create an account with the selected PHR system. At step F1i the patient is asked to add any necessary information to the PHR.

At step F1j the patient who already has a PHR or has just created one is asked if they have already granted access to the provider to access the PHR. For patients who have previously given the provider access to the PHR, the BOLO files are updated at step F1k. For a patient who just created their PHR or has not previously granted the provider access, the patient is asked whether they want to give permission to the provider to update the PHR with information from this visit at step F1l.

If the patient does not wish to have the PHR updated by the provider, the BOLO file is updated to reflect the patients' choice at step F1m.

If the patient wishes to have the PHR updated by the provider with information concerning the current visit, at step F1n the patient is presented with a screen where they can authorize the provider to access the PHR. At step F1o the BOLO file is updated after a patient grants the provider permission to access the PHR. For patients who do not want their PHR updated by the provider, a blank registration template is created at step F1p. For patients who granted the provider access to the PHR a regular registration template with PHR information is created at step F1q.

At step F1r patient registration in the provider's system is completed. At step F1s the patient is asked if they want a copy of the current visit's details automatically sent to the PHR by the provider. If yes, the BOLO file is updated to reflect the patient's desires. If the patient does not want to automatically have the visit information sent to the PHR, the BOLO file is updated at step F1t.

FIG. 2 illustrates the use of billing files with the PHR. At step F1a the providers' billing system releases electronic billing files for submission to the payers. At step F2b all billing files are sent for payment to the appropriate payer and a copy is sent to the PHR Update system for further processing. The system determines when the billing file is completed at step F2c. Once all bills are generated, they are sent for payment and that process is terminated at step F2d.

At step F2e the system looks at the BOLO file to determine if a patient requested a copy of their visit to be uploaded to the PHR. If the patient did not request an update to their PHR, the bill is skipped and log file is updated at step F2f. If the patient did request that their PHR be updated, a standardized CCR/CCD file is created from the bill details at step F2g. Creating a CCR/CCD file can involve a process in which data is extracted (i.e. electronically extracted) from the billing file such as but not limited too demographic, insurance, provider, referrer, diagnostic and procedural information and converting it to codified information formatted as a standard CCR/CCD record suitable for import into the patient's PHR. At step F2h the CCR/CCD file is sent to the PHR for that particular patient. At step F2i the BOLO and log files are updated to reflect that the PHR was updated with the current visit's details.

The invention preferably uses several components for functioning properly:
1. Patient Interaction through Kiosk, Internet Terminal, or Registrar Workstation;
2. BOLO File storage on network;
3. Internet Connection;
4. Healthcare Provider Computer Billing System; and
5. PHR accessed via the Internet.

With the present invention system and method, the automatic updating of personal health records with appropriate patient consent will provide significant administrative, clinical, and financial benefit to healthcare providers and patients alike, including, but not limited to, the following public benefits:
1. Increased control over access to personal health information;
2. Support for patient wellness activities;
3. Support healthcare decisions and responsibility for care;
4. Allow for more continuity of care across time and providers;
5. Patient validation and verification of accuracy of information in health record;
6. Avoidance of unnecessary or duplicate tests;
7. Reduce adverse drug interactions and allergic reactions;
8. Improve medication compliance;
9. Strengthen communication between patient and providers;
10. Support for wellness and preventive care;
11. Provide convenient access for patients to specific information or services such as lab results, e-visits, and Rx refills;

While the invention has been described and disclosed in certain terms and has disclosed certain embodiments or modifications, persons skilled in the art who have acquainted themselves with the invention, will appreciate that it is not necessarily limited by such terms, nor to the specific embodiments and modification disclosed herein. Thus, a wide variety of alternatives, suggested by the teachings herein, can be practiced without departing from the spirit of the invention, and rights to such alternatives are particularly reserved and considered within the scope of the invention.

What is claimed is:

1. A method for determining whether a patient has a personal health record and obtaining consent to populate the personal health record, said method comprising the steps of:
   (a) electronically communicating with a patient to determine whether the patient has an existing electronically stored personal health record maintained by a specific electronic personal health record service provider;
   (b) electronically receiving information from the patient that either:
   identifies the specific electronic personal health record service provider that the patient already has for digitally storing the patient's existing electronic personal health record; or indicates that the patient does not have an existing specific electronic personal health record service provider to digitally store the patient's electronic personal health record; wherein, in response to receiving information that the patient does not have an existing specific electronic personal health record service provider, electronically receiving information from the patient as to which specific electronic personal health record service provider he or she would like to use to create a new electronic personal health record by selecting one from a list of available specific electronic personal health record service providers provided to the patient; and
   (c) receiving information from the patient as to whether the patient consents to updating his or her existing or new electronic personal health record identified or created in step (b);
   wherein electronic communication with the patient is achieved through a remote internet portal, a remote kiosk or an electronic device at a healthcare provider's location.

2. The method of claim 1 further comprising the step of electronically updating a decision file for the patient with whether or not the patient consented to updating his or her existing or new personal health record.

3. The method of claim 1 wherein electronic communication with the patient is performed at appointment time for the patient with a healthcare provider.

4. The method of claim 1 further comprising the step of electronically providing the patient with a registration template connected with personal health records if the patient consents to having his or her existing or new personal health record updated or electronically providing, the patient with a registration not connected with personal health records if the patient does not provide consent for having his or her existing or new personal health record updated.

5. The method of claim 1 further comprising the step of registering the patient in connection with his or her visit.

6. The method of claim 1 further comprising the step of receiving information from the patient as to whether the patient wishes for detail of the patient's visit to be sent to the patient's existing or new personal health record.

7. The method of claim 6 further comprising the step of electronically updating a digitally stored decision file for the patient with whether or not the patient consented to updating his or her existing or new personal health record with the visit's details.

8. The method of claim 6 further comprising the step of electronically sending information concerning the patient's visit to the patient's existing or new electronic personal health record.

9. A method for determining whether a patient has an electronic personal health record and for updating the patient's electronic personal health record with information from a billing file for the patient and digitally storing the billing information on the electronic personal health record, said method comprising the steps of:
  (a) electronically communicating with a patient to determine whether the patient has an existing electronically stored personal health record maintained by a specific electronic personal health record service provider;
  (b) electronically receiving information from the patient that either:
    identifies the specific electronic personal health record service provider that the patient already has for digitally storing the patient's existing electronic personal health record: or
    indicates that the patient does not have an existing specific electronic personal health record service provider to digitally store the patient's electronic personal health record: wherein, in response to receiving information that the patient does not have an existing specific electronic personal health record service provider, electronically receiving information from the patient as to which specific electronic personal health record service provider he or she would like to use to create a new electronic personal health record by selecting one from a list of available specific electronic personal health record service providers provided to the patient; and
  (c) receiving information from the patient as to whether the patient consents to updating his or her existing or new electronic personal health record identified or created in step (b);
  wherein electronic communication with the patient is achieved through a remote internet portal, a remote kiosk or an electronic device at a healthcare provider's office;
  (d) reviewing by a computer system an electronically stored decision file for the patient which contains decisions made by the patient in connection with his or her electronic personal health record to determine whether the patient has consented to updating his Or her personal electronic health record with information concerning a patient's current visit and with billing information for the visit;
  (e) creating an electronically stored billing file from billing records for the patient; and
  (f) electronically forwarding the billing file to the patient's electronic personal health record to update the electronic personal health record to include and electronically store information from the billing file.

10. The method of claim 9 further comprising the step of updating the electronically stored decision file for the patient when a billing file is not sent to the patient's electronic personal health record.

11. The method of claim 9 further comprising the step of updating the electronically stored decision file for the patient concerning the forwarding of the billing file to the patient's electronic personal health record.

12. The method of claim 9 wherein step (b) comprises the step of creating a standardized clinical health record (CCR or CCD file) from a billing, record for the patient.

13. The method of claim 12 wherein the standardized clinical health record is created by electronically extracting information from the billing record and converting the extracted information to codified information formatted as a standard CCR/CCD electronic record suitable for importing into the patient's electronic personal health record.

14. The method of claim 13 further comprising, the step of sending the CCR/CCD file to the patient's electronic, personal health record to update the patient's electronic personal health record with the information from the CCR/CCD file.

15. The method of claim 14 further comprising the step of updating the patient's electronically stored decision file to reflect that the patient's electronic personal health record was electronically updated with the details of the current visit.

\* \* \* \* \*